US011089950B2

(12) United States Patent
Miyake et al.

(10) Patent No.: US 11,089,950 B2
(45) Date of Patent: Aug. 17, 2021

(54) ENDOSCOPE APPARATUS, ACTIVATION METHOD, AND VIDEO PROCESSOR FOR DETERMINING AN ABNORMALITY

(71) Applicant: OLYMPUS CORPORATION, Hachioji (JP)

(72) Inventors: Kensuke Miyake, Tokyo (JP); Takashi Saito, Tokyo (JP); Ryu Oshima, Tokyo (JP); Masahiro Katakura, Tokyo (JP); Yugo Koizumi, Kanagawa (JP); Mai Ojima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 217 days.

(21) Appl. No.: 16/414,863

(22) Filed: May 17, 2019

(65) Prior Publication Data

US 2019/0269308 A1     Sep. 5, 2019

Related U.S. Application Data

(63) Continuation of application No. PCT/JP2017/033397, filed on Sep. 15, 2017.

(30) Foreign Application Priority Data

Nov. 17, 2016   (JP) .............................. JP2016-223891

(51) Int. Cl.
*A61B 1/00*    (2006.01)
*A61B 1/04*    (2006.01)
(Continued)

(52) U.S. Cl.
CPC ................ *A61B 1/015* (2013.01); *A61B 1/00* (2013.01); *A61B 1/00006* (2013.01);
(Continued)

(58) Field of Classification Search
None
See application file for complete search history.

(56) References Cited

U.S. PATENT DOCUMENTS 4,548,197 A   10/1985   Kinoshita
5,951,462 A    9/1999   Yamanaka
(Continued)

FOREIGN PATENT DOCUMENTS

EP   0 082 950 A2    7/1983
EP   0 120 454 A1   10/1984
(Continued)

OTHER PUBLICATIONS

Dec. 12, 2017 International Search Report issued in International Patent Application No. PCT/JP2017/033397.

*Primary Examiner* — John P Leubecker
(74) *Attorney, Agent, or Firm* — Oliff PLC

(57) ABSTRACT

An endoscope apparatus including a connector included in an endoscope and connected to an endoscope connection portion of a video processor, a fluid feeding apparatus including a tube configured to transmit fluid to the endoscope, a connection detector configured to detect a connection state of the tube with the connector of the endoscope, a control unit configured to detect an ON/OFF state of a power source of the fluid feeding apparatus, determine an abnormality exists when the connection detector detects that the tube is in a disconnected state with the connector of the endoscope and the power source of the fluid feeding apparatus is detected to be in an ON state, and output a notification of the determined abnormality, and a display configured to display the notification of the abnormality outputted by the control unit.

9 Claims, 20 Drawing Sheets

(51) Int. Cl.
    *A61B 1/015*    (2006.01)
    *A61B 1/06*     (2006.01)
    *G02B 23/24*    (2006.01)

(52) U.S. Cl.
    CPC ...... *A61B 1/00043* (2013.01); *A61B 1/00055* (2013.01); *A61B 1/00057* (2013.01); *A61B 1/00059* (2013.01); *A61B 1/00119* (2013.01); *A61B 1/00128* (2013.01); *A61B 1/04* (2013.01); *A61B 1/0676* (2013.01); *G02B 23/24* (2013.01)

(56) References Cited

U.S. PATENT DOCUMENTS

| | | | | |
|---|---|---|---|---|
| 2002/0064479 | A1* | 5/2002 | Nakanishi | A61B 1/123 422/28 |
| 2008/0242929 | A1* | 10/2008 | Ito | A61B 1/05 600/114 |
| 2008/0262310 | A1* | 10/2008 | Kawai | A61B 1/00039 600/152 |
| 2015/0070019 | A1* | 3/2015 | Kawakami | A61B 17/3203 324/418 |

FOREIGN PATENT DOCUMENTS

| | | |
|---|---|---|
| JP | S58-086133 A | 5/1983 |
| JP | S59-181119 A | 10/1984 |
| JP | S59-203531 A | 11/1984 |
| JP | H11-169338 A | 6/1999 |
| JP | 2006-116000 A | 5/2006 |
| JP | 2010-005005 A | 1/2010 |
| WO | 2018/092399 A1 | 5/2018 |

* cited by examiner

| WATER FEEDING TUBE | POWER SOURCE OF WATER FEEDING APPARATUS | NOTIFY |
|---|---|---|
| CONNECTED | ON | NO |
| | OFF | YES |
| NOT CONNECTED | ON | YES |
| | OFF | NO |

| THERE IS CONNECTION PORTION | POWER SOURCE OF WATER FEEDING APPARATUS | NOTIFY |
|---|---|---|
| YES | — | NO |
| NO | ON | YES |
| | OFF | NO |

FIG. 12

| WATER FEEDING TUBE | POWER SOURCE OF WATER FEEDING APPARATUS | TYPE OF TRANSMISSION SIGNAL | NOTIFY |
|---|---|---|---|
| CONNECTED | ON | WATER FEEDING PERMISSION SIGNAL | NO |
| CONNECTED | OFF | — | YES |
| NOT CONNECTED | ON | WATER FEEDING PROHIBITION SIGNAL | YES |
| NOT CONNECTED | OFF | — | NO |

FIG. 15

| THERE IS CONNECTION PORTION | POWER SOURCE OF WATER FEEDING APPARATUS | TYPE OF TRANSMISSION SIGNAL | NOTIFY |
|---|---|---|---|
| YES | — | — | NO |
| NO | ON | WATER FEEDING PROHIBITION SIGNAL | YES |
| | OFF | — | NO |

FIG. 17

| THERE IS CONNECTION PORTION | WATER FEEDING TUBE | POWER SOURCE OF WATER FEEDING APPARATUS | NOTIFY |
|---|---|---|---|
| YES | CONNECTED | ON | NO |
| | | OFF | YES |
| | NOT CONNECTED | ON | YES |
| | | OFF | NO |
| NO | — | ON | YES |
| | | OFF | NO |

FIG. 20

| THERE IS CONNECTION PORTION | WATER FEEDING TUBE | POWER SOURCE OF WATER FEEDING APPARATUS | TYPE OF TRANSMISSION SIGNAL | NOTIFICATION |
|---|---|---|---|---|
| YES | CONNECTED | ON | WATER FEEDING PERMISSION SIGNAL | NO |
| | | OFF | — | YES |
| | NOT CONNECTED | ON | WATER FEEDING PROHIBITION SIGNAL | YES |
| | | OFF | — | NO |
| NO | — | ON | WATER FEEDING PROHIBITION SIGNAL | YES |
| | | OFF | — | NO |

ENDOSCOPE APPARATUS, ACTIVATION METHOD, AND VIDEO PROCESSOR FOR DETERMINING AN ABNORMALITY

CROSS REFERENCE TO RELATED APPLICATION

This application is a continuation application of PCT/JP2017/033397 filed on Sep. 15, 2017 and claims benefit of Japanese Application No. 2016-223891 filed in Japan on Nov. 17, 2016, the entire contents of which are incorporated herein by this reference.

BACKGROUND

1. Field of the Invention

The exemplary embodiments relate to an endoscope apparatus that detects a connection state of a tube connected to an endoscope, an activation method of an endoscope apparatus, and a video processor.

2. Description of the Related Art

An endoscope apparatus including an endoscope that picks up an image of an object in a subject, a video processor that generates an observation image of the object, an image of which is picked up by the endoscope, and a monitor that displays the observation image generated by the video processor has been widely used in a medical field, an industrial field, and the like.

The endoscope used in the medical field can observe an inside of a body cavity that is the subject by inserting an elongated insertion portion into the body cavity, and can perform various types of treatments and the like with use of a treatment instrument inserted in an insertion channel for the treatment instrument included in the endoscope, as necessary. One example of an endoscope includes a liquid feeding pipe line for supplying liquid such as water or an air feeding pipe line for supplying air or gas such as carbon dioxide gas in the insertion portion in addition to the insertion channel for the treatment instrument.

The liquid, such as water, is supplied into the water feeding pipe line from a water feeding pipe sleeve included in an endoscope connector, and is ejected toward an observation window and the like from a nozzle provided on a distal end portion of the insertion portion, or toward a section to be observed from a discharge port provided in the distal end portion of the insertion portion. Therefore, in this exemplary endoscope, a water feeding apparatus for supplying the liquid such as water is connected via a water feeding tube.

For example, Japanese Patent Application Laid-Open Publication No. 2006-116000 discloses a liquid storage apparatus for endoscope that detects an electrical connection between a processor and a storage apparatus, detects an amount of storage water when the processor and the storage apparatus are electrically connected to each other, and provides a warning indicating that the amount of storage water is small when the amount of storage water is equal to or less than a minimum storage amount.

SUMMARY

An endoscope apparatus of one aspect of an exemplary embodiment includes a connector included in an endoscope and connected to an endoscope connection portion of a video processor, a fluid feeding apparatus including a tube configured to transmit fluid to the endoscope, a connection detector configured to detect a connection state of the tube with the connector of the endoscope, a control unit configured to detect an ON/OFF state of a power source of the fluid feeding apparatus, determine an abnormality exists when the connection detector detects that the tube is in a disconnected state with the connector of the endoscope and the power source of the fluid feeding apparatus is detected to be in an ON state, and output a notification of the determined abnormality, and a display configured to display the notification of the abnormality outputted by the control unit.

A video processor of one aspect of an exemplary embodiment includes a control unit that is configured to acquire (i) information indicating whether a tube of the endoscope configured to supply the fluid from the water feeding apparatus is in a connected state or a disconnected state with respect to the endoscope and (ii) information on whether a power source of the water feeding apparatus is in an ON state or an OFF state, determine an abnormality exists when the tube is in the disconnected state and the power source is in the ON state based on the acquired information, and control a display to display a notification in response to determine that the abnormality exists.

An activation method of an endoscope apparatus of an exemplary embodiment is an activation method of an endoscopic apparatus including a connector included in an endoscope and connected to an endoscope connection portion of a video processor, and a fluid feeding apparatus including a tube connected to the connector and configured to supply fluid to the endoscope. The activation method includes a step of transmitting the fluid to the endoscope via the tube by the fluid feeding apparatus, a step of detecting a connection state of the tube with the connector by a connection detector, a step of detecting an ON/OFF state of a power source of the fluid feeding apparatus by a control unit, a step of determining an abnormality exists when the connection detector detects that the tube is in a disconnected state with the connector of the endoscope and the power source of the fluid feeding apparatus is detected to be in an ON state, and a step of outputting a notification of the determined abnormality.

BRIEF DESCRIPTION OF THE DRAWINGS

FIG. 12 is a diagram for describing a relationship among the connection state of the water feeding tube 33, the state of the power source of the water feeding apparatus 30, a type of a transmission signal, and the notification of abnormality;

FIG. 15 is a diagram for describing a relationship among whether there is a water feeding tube connection portion, the state of the power source of the water feeding apparatus 30, the type of the transmission signal, and the notification of abnormality;

FIG. 17 is a diagram for describing a relationship among whether there is a water feeding tube connection portion, the connection state of the water feeding tube 33, the state of the power source of the water feeding apparatus 30, and the notification of abnormality;

FIG. 20 is a diagram for describing a relationship among whether there is a water feeding tube connection portion, the connection state of the water feeding tube 33, the state of the power source of the water feeding apparatus 30, the type of the transmission signal, and the notification of abnormality;

DETAILED DESCRIPTION

Figure 1:
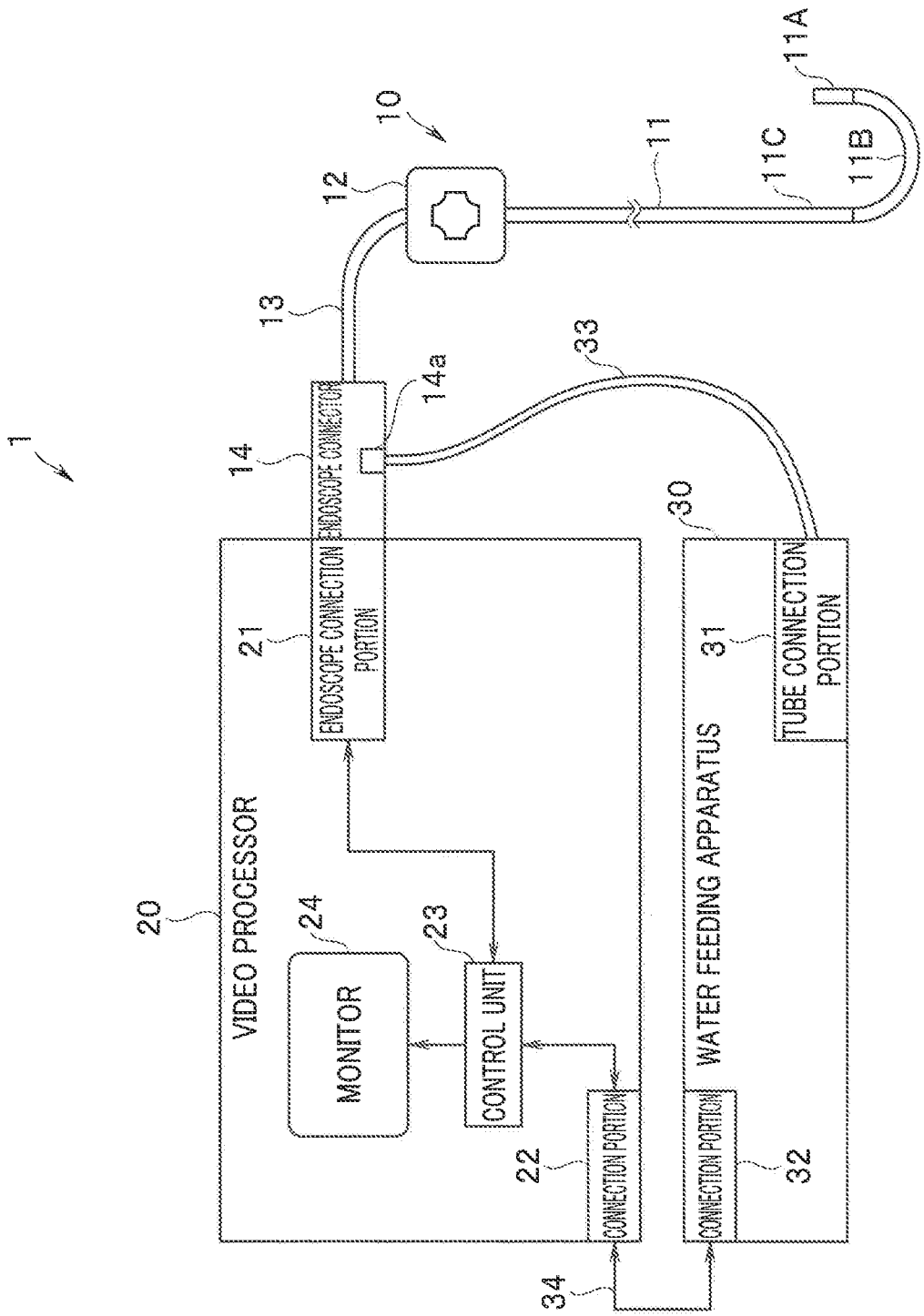
FIG. 1 is a configuration diagram illustrating a configuration of an endoscope apparatus according to Embodiment 1.

Exemplary embodiments are described in detail below with reference to the drawings.

Note that each of the drawings used in the description below is schematically illustrated, and a dimensional relationship, a scale, and the like of each member may be illustrated so as to be different for each constituent element in order to illustrate each constituent element in a recognizable manner in the drawings. Therefore, the exemplary embodiments are not only limited to the illustrated forms such as the number of the constituent elements, a shape of the constituent element, a size ratio of the constituent element, and a relative position of each constituent element illustrated in the drawings.

Embodiment 1

FIG. 1 is a configuration diagram illustrating a configuration of an endoscope apparatus according to Embodiment 1.

The endoscope apparatus 1 illustrated in FIG. 1 includes an endoscope 10 that is inserted in a subject and picks up an image of an object such as a biological tissue in the subject, a video processor 20 that generates an endoscope image such as an observation image by performing predetermined signal processing on an image pickup signal, an image of which is picked up by the endoscope 10, and a water feeding apparatus 30 serving as a fluid transmitting unit that transmits fluid such as water to the endoscope 10.

Note that the endoscope apparatus 1 may include a display apparatus that is connected to the video processor 20 by a connection cable and the like and displays an observation image and the like generated by the video processor 20. In the video processor 20, a light source apparatus (not shown) that supplies illumination light for observation is provided in the endoscope 10 in an integrated manner, but the endoscope apparatus 1 may include a light source apparatus that is a separate body from the video processor 20.

The endoscope 10 includes an insertion portion 11 inserted into the subject, an operation portion 12 provided on a proximal end side of the insertion portion 11, and a universal cord 13 extending from the operation portion 12. The universal cord 13 includes, on a distal end, an endoscope connector 14 serving as a connection portion that is removably connected to the video processor 20. The endoscope connector 14 includes a connection detecting unit 14a that detects a connection of a water feeding tube 33 described below from the water feeding apparatus 30.

The insertion portion 11 inserted into the subject includes a distal end portion 11A, a bending portion 11B freely bendable in vertical and horizontal directions, and a pliant flexible tube portion 11C having flexibility in the order from a distal end side. The operation portion 12 includes an operation knob for performing bending operation of the bending portion 11B, an operation switch for performing various types of operation of the endoscope 10, and the like.

The video processor 20 includes an endoscope connection portion 21 to which the endoscope connector 14 is connected, a connection portion 22 electrically connected to the water feeding apparatus 30, a control unit 23 that performs an entire control of the video processor 20, and a monitor 24 (notification unit) such as an LCD that displays various types of operation screens and provides a notification of abnormality, for example, based on the control by the control unit 23.

The water feeding apparatus 30 includes a tube connection portion 31 to which the water feeding tube 33 that is a tube for transmitting fluid such as water is connected, and a connection portion 32 electrically connected to the video processor 20. The water feeding tube 33 connected to the tube connection portion 31 is connected to the endoscope connector 14 via a water feeding pipe sleeve (not shown) and the like provided on the endoscope connector 14. The connection portion 22 of the video processor 20 and the connection portion 32 of the water feeding apparatus 30 are electrically connected to each other via an electric cable 34.

The connection detecting unit 14a detects whether the water feeding tube 33 is connected to the endoscope connector 14, and outputs the detection result to the control unit 23 via the endoscope connection portion 21. In other words, the connection detecting unit 14a forms a tube connection state detecting unit that detects the connection state of the water feeding tube 33 with respect to the endoscope connector 14. A method of detecting the connection of the water feeding tube 33 by the connection detecting unit 14a is, for example, detection using a microswitch that opens and closes by being pressed down when the water feeding tube 33 is connected. Note that the method of detecting the connection is not limited to a detection method using the microswitch, and the detection may be performed with use of a light sensor that detects the blocking of light when the water feeding tube 33 is connected or an electrical contact that detects an electrical connection between the water feeding tube 33 and the endoscope connector 14, for example.

To the control unit 23, ON/OFF information of the power source of the water feeding apparatus 30 is inputted. The ON/OFF information of the power source of the water feeding apparatus 30 is inputted to the control unit 23 via the connection portion 32, the electric cable 34, and the connection portion 22. As described above, the control unit 23 forms a power source state detecting unit that detects an ON/OFF state of the power source of the water feeding apparatus 30.

The control unit 23 determines whether there is an abnormality according to the detection result from the connection detecting unit 14a and the ON/OFF information of the power source of the water feeding apparatus 30, and performs control such that a notification of abnormality is provided with use of the monitor 24. The notification of abnormality is provided by displaying a message informing the abnormality on the monitor 24, for example. Note that the notification of abnormality is not limited to the display of the message informing the abnormality on the monitor 24, and, for example, notification may be provided by a buzzer sound, a voice, and the like, or notification may be provided by lighting of an LED and the like.

Figures 2, 3:
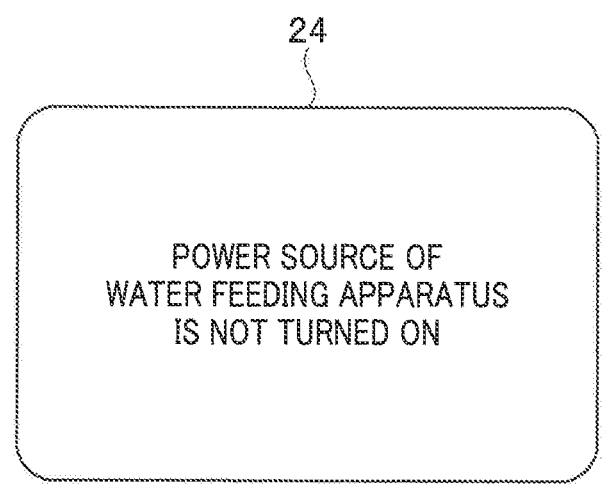
FIG. 2 is a diagram for describing a relationship among a connection state of a water feeding tube 33, a state of a power source of a water feeding apparatus 30, and a notification of abnormality.
FIG. 3 is a view illustrating an example of a notification screen at the time of an abnormality.
Figure 4:
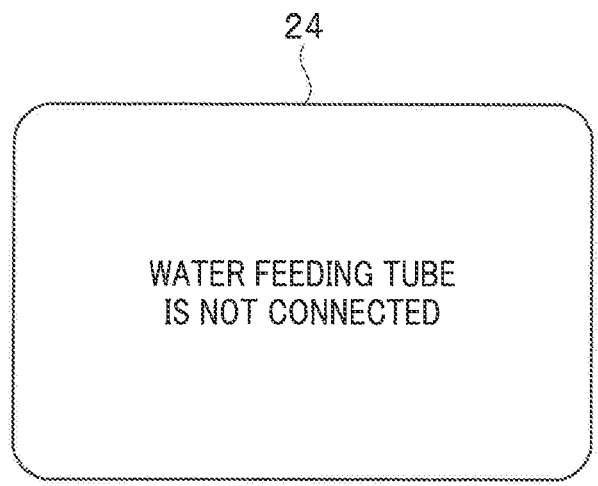
FIG. 4 is a view illustrating another example of a notification screen at the time of an abnormality.

Specific examples of the notification of abnormality and notification screens at the time of an abnormality displayed on the monitor 24 are described with reference to FIG. 2 to FIG. 4. FIG. 2 is a diagram for describing a relationship among the connection state of the water feeding tube 33, the state of the power source of the water feeding apparatus 30, and the notification of abnormality, FIG. 3 is a view illustrating an example of a notification screen at the time of an abnormality, and FIG. 4 is a view illustrating another example of a notification screen at the time of an abnormality.

As shown in FIG. 2, the control unit 23 does not provide the notification of abnormality when the water feeding tube 33 is connected to the endoscope connector 14 and the power source of the water feeding apparatus 30 is ON. When the water feeding tube 33 is connected to the endoscope connector 14 and the power source of the water feeding apparatus 30 is ON, a user can use a water feeding function without problems. Therefore, the control unit 23 determines that there is no abnormality and does not provide the notification of abnormality when the water feeding tube 33 is connected to the endoscope connector 14 and the power source of the water feeding apparatus 30 is ON.

The control unit 23 provides the notification of abnormality when the water feeding tube 33 is connected to the endoscope connector 14 and the power source of the water feeding apparatus 30 is OFF. The user is conceived to be desiring to use the water feeding function because the water feeding tube 33 is connected to the endoscope connector 14, but the water feeding function cannot be used because the power source of the water feeding apparatus 30 is OFF. Therefore, when the water feeding tube 33 is connected to the endoscope connector 14 and the power source of the water feeding apparatus 30 is OFF, the control unit 23 determines that there is an abnormality and causes the monitor 24 to display a message informing the abnormality, that is, "power source of water feeding apparatus is not turned on" as illustrated in FIG. 3.

The control unit 23 provides the notification of abnormality when the water feeding tube 33 is not connected to the endoscope connector 14 and the power source of the water feeding apparatus 30 is ON. The water feeding function can be used because the power source of the water feeding apparatus 30 is ON. However, the water feeding tube 33 is not connected to the endoscope connector 14, and hence there is a fear that water is fed to unintended places such as equipment, an examination room floor, a staff, and a patient. Therefore, when the water feeding tube 33 is not connected to the endoscope connector 14 and the power source of the water feeding apparatus 30 is ON, the control unit 23 determines that there is an abnormality and causes the monitor 24 to display a message informing the abnormality, that is, "water feeding tube is not connected" as illustrated in FIG. 4.

The control unit 23 does not provide the notification of abnormality when the water feeding tube 33 is not connected to the endoscope connector 14 and the power source of the water feeding apparatus 30 is OFF. When the water feeding tube 33 is not connected to the endoscope connector 14 and the power source of the water feeding apparatus 30 is OFF, it is conceived that the user does not use the water feeding function. Therefore, when the water feeding tube 33 is not connected to the endoscope connector 14 and the power source of the water feeding apparatus 30 is OFF, the control unit 23 determines that there is no abnormality and does not provide the notification of abnormality.

Next, the operation of the endoscope apparatus 1 formed as above is described.

Figure 5:
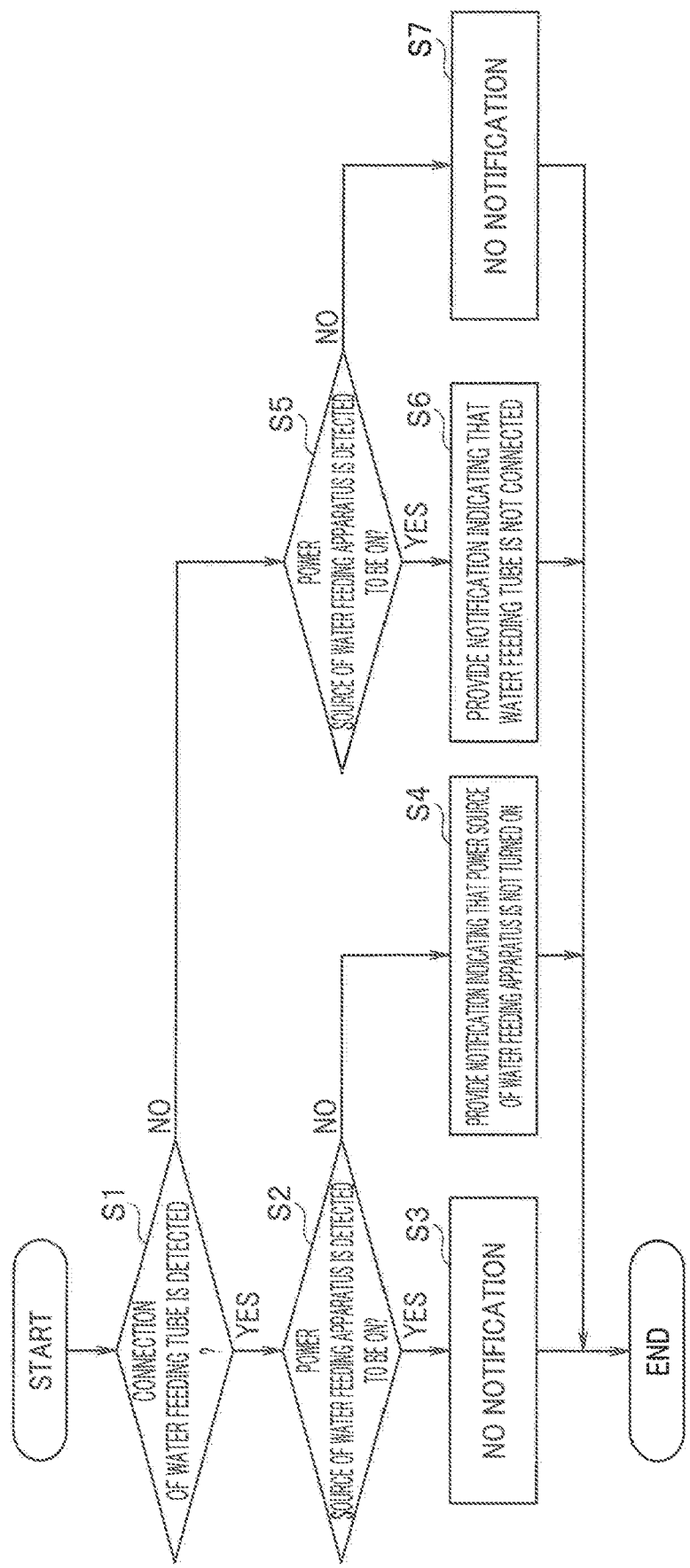
FIG. 5 is a flowchart illustrating an example of a flow of abnormality detection processing performed by the endoscope apparatus of Embodiment 1.

FIG. 5 is a flowchart illustrating an example of a flow of abnormality detection processing performed by the endoscope apparatus of Embodiment 1.

First, the control unit 23 determines whether the water feeding tube 33 is connected to the endoscope connector 14 (S1). The determination is performed based on the detection result from the connection detecting unit 14a. When the control unit 23 determines that the water feeding tube 33 is connected to the endoscope connector 14 (S1: YES), the control unit 23 determines whether the power source of the water feeding apparatus 30 is ON (S2). The determination is performed based on the ON/OFF information of the power source from the water feeding apparatus 30.

When the control unit 23 determines that the power source of the water feeding apparatus 30 is ON (S2: YES), the control unit 23 does not perform notification (S3) and ends the processing. When the control unit 23 determines that the power source of the water feeding apparatus 30 is not ON (S2: NO), the control unit 23 provides a notification indicating that the power source of the water feeding apparatus 30 is not turned on (S4) and ends the processing.

In Step S1, when the control unit 23 determines that the water feeding tube 33 is not connected to the endoscope connector 14 (S1: NO), the control unit 23 determines whether the power source of the water feeding apparatus 30 is ON (S5). When the control unit 23 determines that the power source of the water feeding apparatus 30 is ON (S5: YES), the control unit 23 provides a notification indicating that the water feeding tube 33 is not connected (S6) and ends the processing. When the control unit 23 determines that the power source of the water feeding apparatus 30 is not ON (S5: NO), the control unit 23 does not perform the notification (S7) and ends the processing.

Note that the processing in FIG. 5 is constantly executed while the power source of the endoscope apparatus 1 is ON, and notification is performed when there is an abnormality. In the processing in FIG. 5, it is detected that the power source of the water feeding apparatus 30 is ON after the connection of the water feeding tube 33 is detected, but the connection of the water feeding tube 33 may be detected after the power source of the water feeding apparatus 30 is detected to be ON. In other words, an execution order of the respective steps in the flowchart in FIG. 5 may be changed, a plurality of the respective steps in the flowchart in FIG. 5 may be simultaneously executed, or the respective steps in the flowchart in FIG. 5 may be executed in an order that is different for each execution as long as the execution is not contrary to the nature of the steps. Note that similarly in flowcharts described hereinafter, processing illustrated in the flowchart is constantly executed while the power source of the endoscope apparatus 1 is ON and notification is performed when there is an abnormality. Similarly in the flowcharts described hereinafter, an execution order of the respective steps may be changed, a plurality of the respective steps may be simultaneously executed, or the respective steps may be executed in an order that is different for each execution as long as the execution is not contrary to the nature of the steps.

As described above, in the endoscope apparatus 1, a notification of abnormality is provided according to whether the water feeding tube 33 is connected to the endoscope connector 14 and whether the power source of the water feeding apparatus 30 is ON. As a result, a case where water feeding is performed when the water feeding tube 33 is not connected to the endoscope connector 14 does not occur when the user checks the abnormality, a notification of which is provided from the endoscope apparatus 1. A case where the water feeding cannot be performed even when the water feeding tube 33 is connected to the endoscope connector 14 because the power source of the water feeding apparatus 30 is OFF can be prevented when the user checks the abnormality, a notification of which is provided from the endoscope apparatus 1.

Therefore, according to the endoscope apparatus of the present embodiment, a notification of abnormality can be provided by detecting the connection state of the water feeding tube with respect to the endoscope connector and the state of the power source of the water feeding apparatus.
(Modification)

Next, a modification of Embodiment 1 is described.

The user checks whether the water feeding function can be used without problems in a preparation stage before performing the examination using the endoscope apparatus 1. In other words, the user checks whether fluid such as water is transmitted from the water feeding tube 33 in a state in which the water feeding tube 33 is not connected to the endoscope connector 14.

At that time, the video processor 20 provides the notification of abnormality because the water feeding tube 33 is not connected to the endoscope connector 14 and the power source of the water feeding apparatus 30 is ON. However, the water feeding is intentionally performed by the user in the preparation stage before the examination, and hence it is troublesome for the user when the notification of abnormality is provided.

Thus, the control unit 23 does not provide the notification of abnormality when it is detected that the operation is in the preparation stage before the examination. Note that in order to indicate that the operation is in the preparation stage before the examination, a signal indicating that the operation is in the preparation stage only needs to be transmitted to the control unit 23 by operating various types of operation buttons and the like provided on the video processor 20 by the user, for example.

Figure 6:
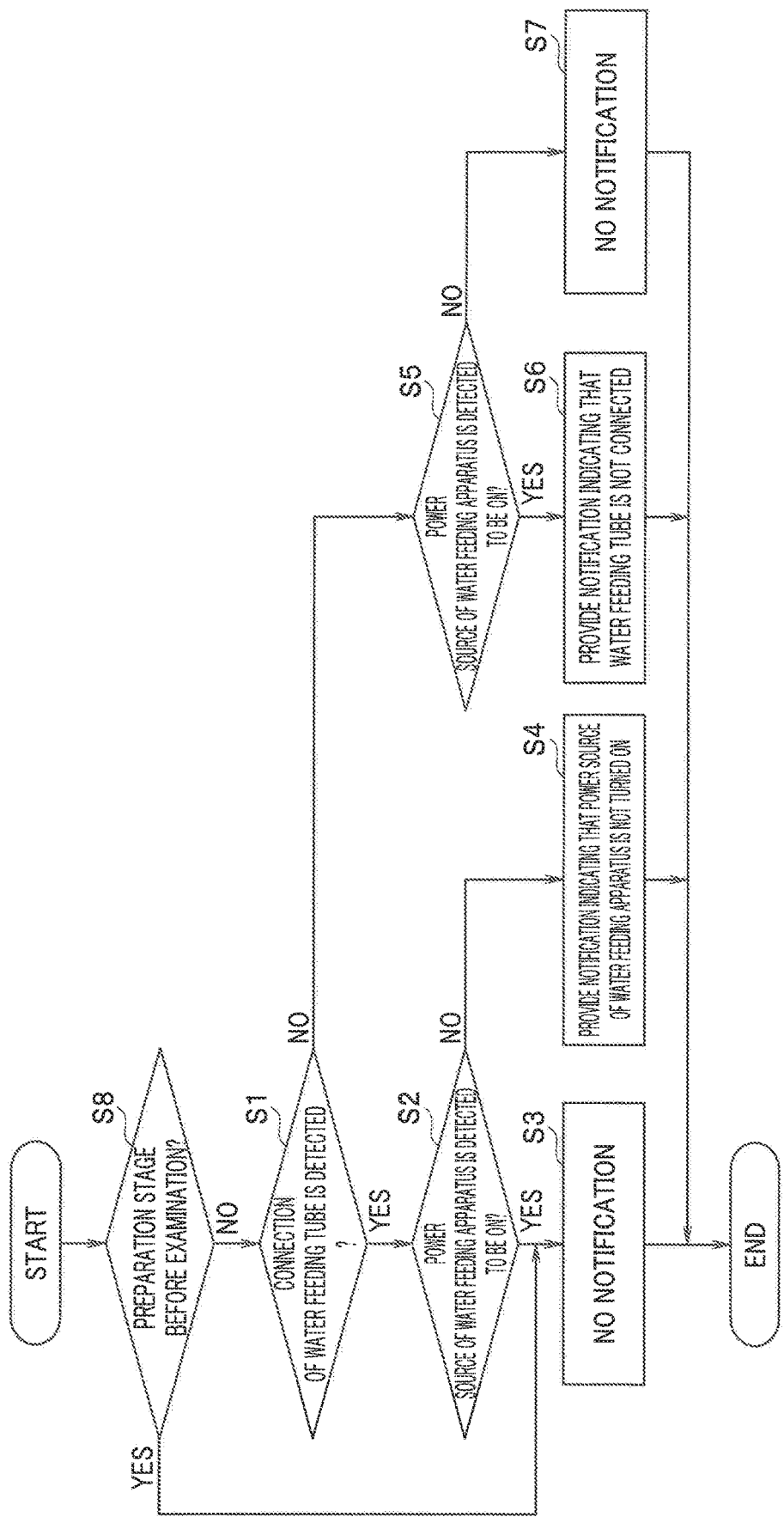
FIG. 6 is a flowchart illustrating an example of a flow of abnormality detection processing performed by an endoscope apparatus of a modification.

FIG. 6 is a flowchart illustrating an example of a flow of abnormality detection processing performed by the endoscope apparatus of the modification. Note that in FIG. 6, processing similar to the processing in FIG. 5 is denoted by the same reference characters and a description of the processing is omitted.

First, the control unit 23 determines whether the operation is in the preparation stage before the examination (S8). When the control unit 23 determines that the operation is in the preparation stage before the examination (S8: YES), the control unit 23 proceeds to Step S3 and ends the processing without performing the notification of abnormality. When the control unit 23 determines that the operation is not in the preparation stage before the examination (S8: NO), the control unit 23 proceeds to Step S1 and executes processing similar to the processing in Embodiment 1.

By the processing above, the endoscope apparatus 1 is prevented from performing the notification of abnormality when the water feeding function is checked in the preparation stage before the examination. Note that the processing in the modification can be applied to endoscope apparatuses in Embodiment 2 and embodiments after Embodiment 2 described below.

Embodiment 2

Next, Embodiment 2 is described.

Figure 7:
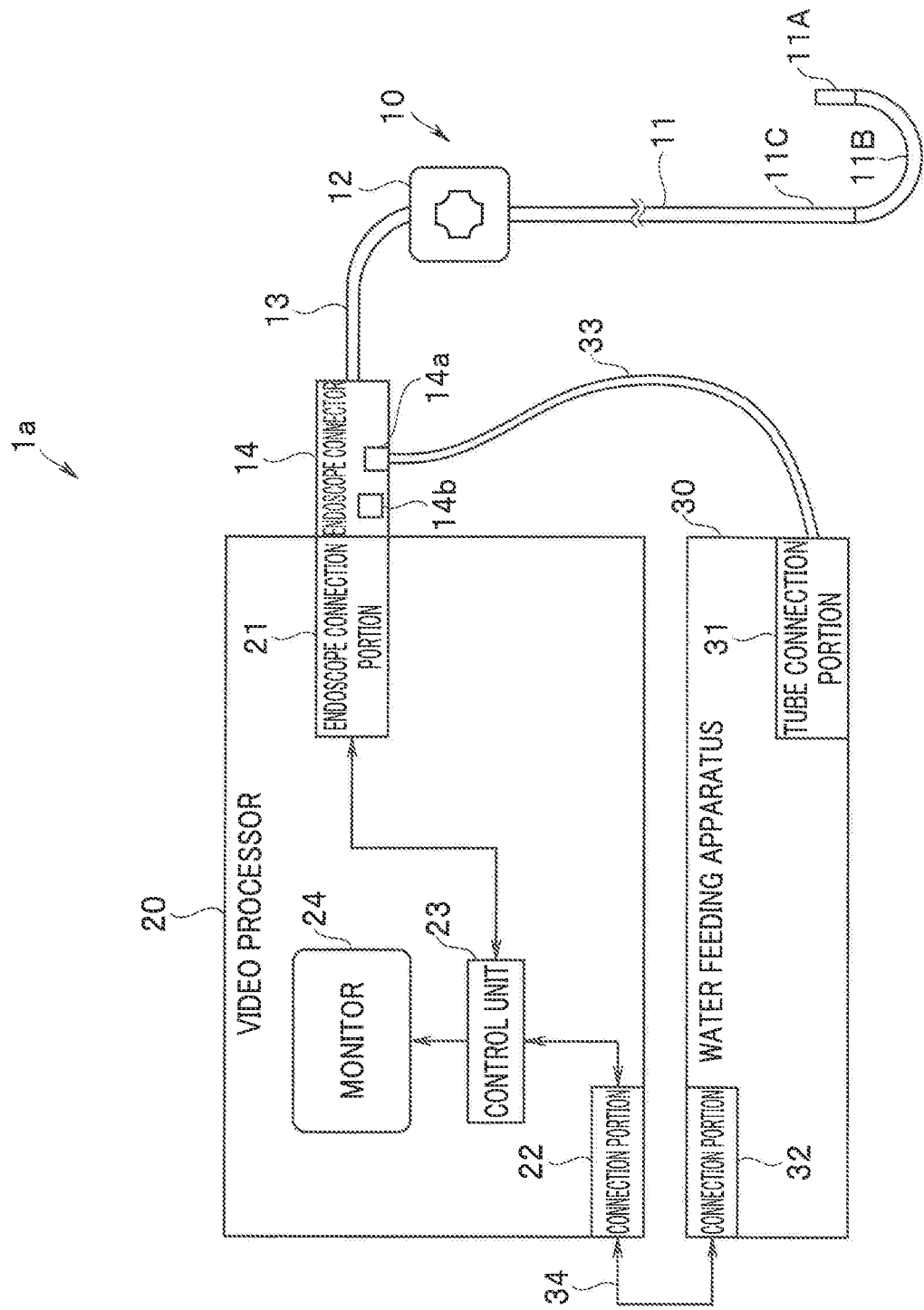
FIG. 7 is a configuration diagram illustrating a configuration of an endoscope apparatus according to Embodiment 2.

FIG. 7 is a configuration diagram illustrating a configuration of an endoscope apparatus according to Embodiment 2. Note that in FIG. 7, configurations similar to the configurations in FIG. 1 are denoted by the same reference characters and a description of the configurations is omitted.

As illustrated in FIG. 7, an endoscope apparatus 1a includes, in the endoscope connector 14 of the endoscope 10, a storage unit 14b in which a scope ID such as type information of the endoscope is stored.

When the endoscope connector 14 is connected to the endoscope connection portion 21, the control unit 23 of the video processor 20 reads out the scope ID from the storage unit 14b and acquires the type information of the connected endoscope 10. As described above, the control unit 23 forms an endoscope type determination unit that determines the type of the endoscope 10.

The control unit 23 determines whether the connected endoscope 10 includes a water feeding tube connection portion for connecting the water feeding tube 33 based on the acquired type information of the endoscope 10. The control unit 23 determines whether there is an abnormality according to whether there is a water feeding tube connection portion in the endoscope connector 14 and information on ON/OFF of the power source of the water feeding apparatus 30 and provides a notification of abnormality with use of the monitor 24.

Note that the storage unit 14b may store information on whether the water feeding tube connection portion is included in the endoscope connector 14, and the control unit 23 may read out the information on whether the water feeding tube connection portion is included from the storage unit 14b when the endoscope connector 14 is connected to the endoscope connection portion 21.

Figures 8, 9:
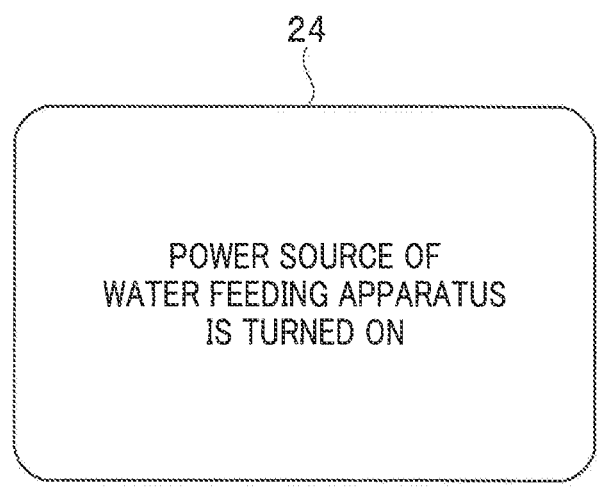
FIG. 8 is a diagram for describing a relationship among whether there is a water feeding tube connection portion, the state of the power source of the water feeding apparatus 30, and the notification of abnormality.
FIG. 9 is a view illustrating an example of the notification screen at the time of an abnormality.

Now, specific examples of the notification of abnormality and the notification screen displayed on the monitor 24 at the time of an abnormality are described with reference to FIG. 8 and FIG. 9. FIG. 8 is a diagram for describing a relationship among whether there is a water feeding tube connection portion, the state of the power source of the water feeding apparatus 30, and the notification of abnormality, and FIG. 9 is a view illustrating an example of the notification screen at the time of an abnormality.

As shown in FIG. 8, the control unit 23 does not provide the notification of abnormality regardless of the ON/OFF of the power source of the water feeding apparatus 30 when there is a water feeding tube connection portion in the endoscope connector 14.

The control unit 23 provides the notification of abnormality when there is no water feeding tube connection portion in the endoscope connector 14 and the power source of the water feeding apparatus 30 is ON. When there is no water feeding tube connection portion in the endoscope connector 14 and the power source of the water feeding apparatus 30 is ON, there is a fear that water is fed to unintended places. Therefore, when there is no water feeding tube connection portion in the endoscope connector 14 and the power source of the water feeding apparatus 30 is ON, the control unit 23 causes the monitor 24 to display the message informing the abnormality, that is, "power source of water feeding apparatus is turned on" as illustrated in FIG. 9.

When there is no water feeding tube connection portion in the endoscope connector 14 and the power source of the water feeding apparatus 30 is OFF, the control unit 23 does not provide the notification of abnormality. Even when there is no water feeding tube connection portion in the endoscope connector 14, the user cannot use the water feeding function when the power source of the water feeding apparatus 30 is OFF. Therefore, when there is no water feeding tube connection portion in the endoscope connector 14 and the power source of the water feeding apparatus 30 is OFF, the control unit 23 determines that there is no abnormality and does not provide the notification of abnormality.

Next, the operation of the endoscope apparatus 1a formed as above is described.

Figure 10:
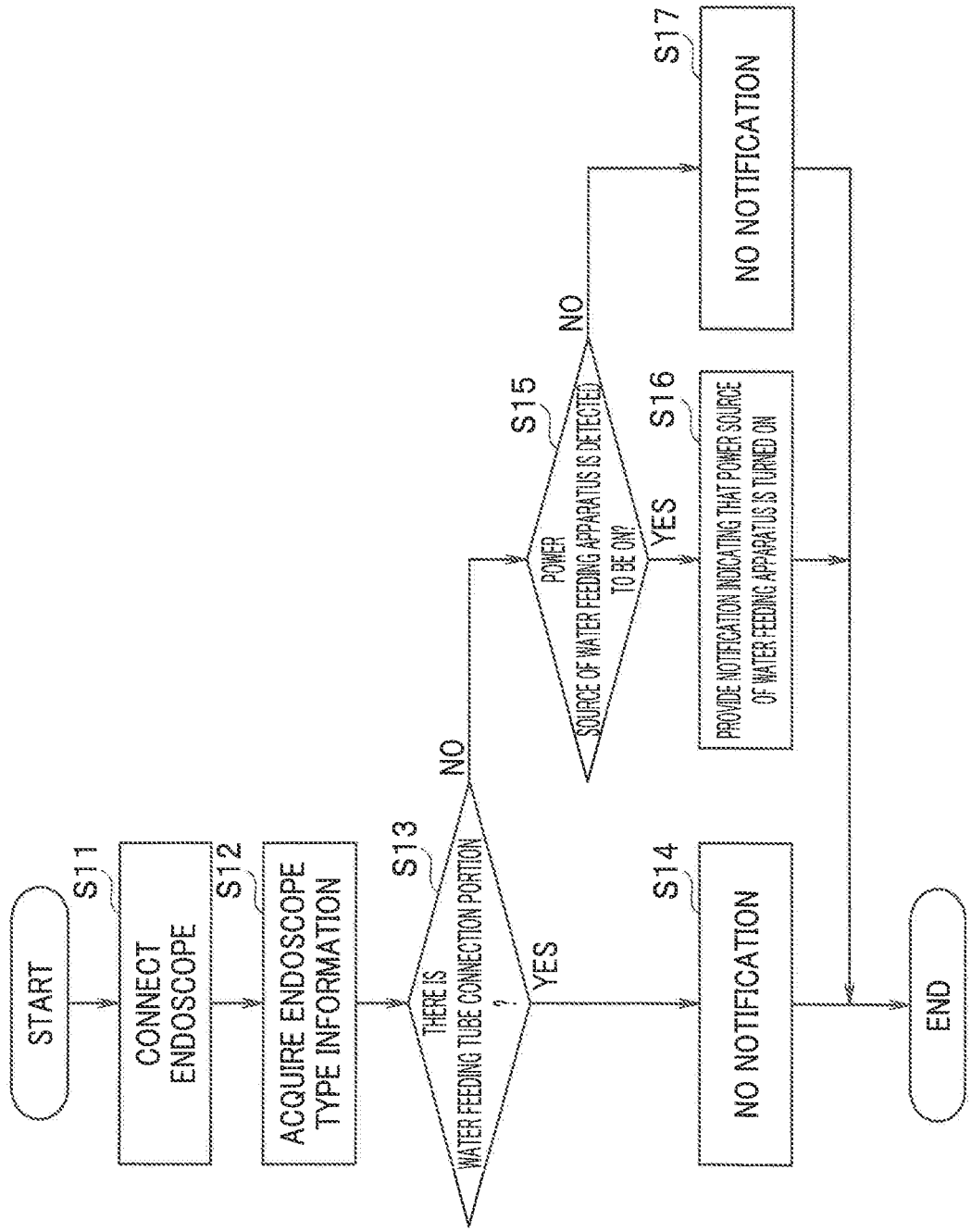
FIG. 10 is a flowchart illustrating an example of a flow of abnormality detection processing performed by the endoscope apparatus of Embodiment 2.

FIG. 10 is a flowchart illustrating an example of a flow of abnormality detection processing performed by the endoscope apparatus of Embodiment 2.

First, the endoscope connector 14 of the endoscope 10 is connected to the endoscope connection portion 21 (S11). When the endoscope connector 14 is connected to the endoscope connection portion 21, the control unit 23 acquires the endoscope type information from the storage unit 14b provided in the endoscope connector 14 (S12).

The control unit 23 determines whether there is a water feeding tube connection portion in the connected endoscope 10 based on the acquired endoscope type information (S13). When the control unit 23 determines that there is a water feeding tube connection portion (S13: YES), the control unit 23 does not perform notification (S14) and ends the processing. When the control unit 23 determines that there is no water feeding tube connection portion (S13: NO), the control unit 23 determines whether the power source of the water feeding apparatus 30 is ON (S15).

When the control unit 23 determines that the power source of the water feeding apparatus 30 is ON (S15: YES), the control unit 23 provides a notification indicating that the power source of the water feeding apparatus 30 is turned on (S16) and ends the processing. When the control unit 23 determines that the power source of the water feeding apparatus 30 is not turned on (S15: NO), the control unit 23 does not perform notification (S17) and ends the processing.

As described above, the endoscope apparatus 1a provides a notification of abnormality according to whether there is a water feeding tube connection portion in the endoscope 10 and whether the power source of the water feeding apparatus 30 is ON. As a result, a case where water feeding is performed when the water feeding tube 33 is not connected to the endoscope connector 14 does not occur when the user checks the abnormality, a notification of which is provided from the endoscope apparatus 1a.

Embodiment 3

Next, Embodiment 3 is described.

Figure 11:
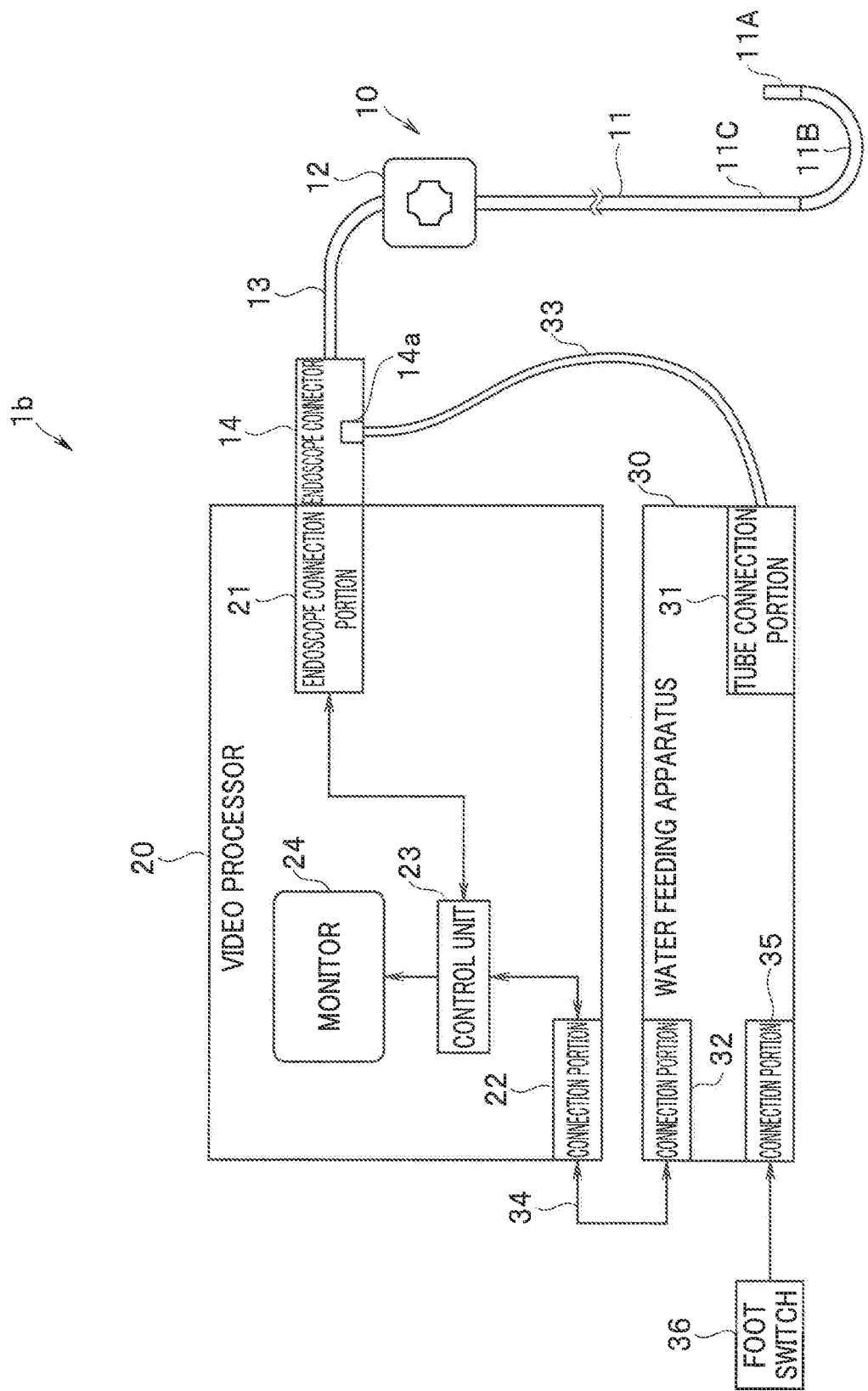
FIG. 11 is a configuration diagram illustrating a configuration of an endoscope apparatus according to Embodiment 3.

FIG. 11 is a configuration diagram illustrating a configuration of an endoscope apparatus according to Embodiment 3. Note that in FIG. 11, configurations similar to the configurations in FIG. 1 are denoted by the same reference characters and a description of the configurations is omitted.

As illustrated in FIG. 11, an endoscope apparatus 1b includes a connection portion 35 to which a foot switch 36 is connected in the water feeding apparatus 30. When the user performs an operation of pressing down the foot switch 36, a water feeding command signal is transmitted to the water feeding apparatus 30. The water feeding apparatus 30 controls the water feeding function to be used or not used based on the water feeding command signal transmitted from the foot switch 36.

The control unit 23 transmits a water feeding permission signal or a water feeding prohibition signal to the water feeding apparatus 30 according to the detection result from the connection detecting unit 14a and the ON/OFF information of the power source of the water feeding apparatus 30. As with Embodiment 1, the control unit 23 determines whether there is an abnormality according to the detection result from the connection detecting unit 14a and the ON/OFF information of the power source of the water feeding apparatus 30, and provides a notification of abnormality to the monitor 24.

Now, specific examples of the connection state of the water feeding tube 33, the state of the power source of the water feeding apparatus 30, the type of the transmission signal, and the notification of abnormality are described with reference to FIG. 12. FIG. 12 is a diagram for describing a relationship among the connection state of the water feeding tube 33, the state of the power source of the water feeding apparatus 30, the type of the transmission signal, and the notification of abnormality. Note that the notification of abnormality is similar to the notification of abnormality in Embodiment 1, and hence the description of the notification of abnormality is omitted.

As shown in FIG. 12, when the water feeding tube 33 is connected to the endoscope connector 14 and the power source of the water feeding apparatus 30 is ON, the control unit 23 transmits the water feeding permission signal to the water feeding apparatus 30. When the water feeding tube 33 is connected to the endoscope connector 14 and the power source of the water feeding apparatus 30 is ON, the user can use the water feeding function without problems. Therefore, the control unit 23 transmits the water feeding permission signal to the water feeding apparatus 30. When the water feeding apparatus 30 receives the water feeding permission signal from the control unit 23 of the video processor 20, the water feeding apparatus 30 executes the water feeding function when the water feeding apparatus 30 receives the water feeding command signal from the foot switch 36.

When the water feeding tube 33 is not connected to the endoscope connector 14 and the power source of the water feeding apparatus 30 is OFF, the control unit 23 does not transmit the water feeding permission signal or the water feeding prohibition signal to the water feeding apparatus 30. When the power source of the water feeding apparatus 30 is OFF, the water feeding apparatus 30 cannot execute the water feeding function. Therefore, the control unit 23 does not transmit the water feeding permission signal or the water feeding prohibition signal to the water feeding apparatus 30.

When the water feeding tube 33 is not connected to the endoscope connector 14 and the power source of the water feeding apparatus 30 is ON, the control unit 23 transmits the water feeding prohibition signal to the water feeding apparatus 30. The water feeding function can be used because the power source of the water feeding apparatus 30 is ON. However, the water feeding tube 33 is not connected to the endoscope connector 14, and hence there is a fear that water is fed to unintended places. Therefore, the control unit 23 transmits the water feeding prohibition signal to the water feeding apparatus 30. When the water feeding apparatus 30 receives the water feeding prohibition signal from the control unit 23 of the video processor 20, the water feeding apparatus 30 does not execute the water feeding function even when the water feeding apparatus 30 receives the water feeding command signal from the foot switch 36.

When the water feeding tube 33 is not connected to the endoscope connector 14 and the power source of the water feeding apparatus 30 is OFF, the control unit 23 does not transmit the water feeding permission signal or the water feeding prohibition signal to the water feeding apparatus 30. When the power source of the water feeding apparatus 30 is OFF, the water feeding apparatus 30 cannot execute the water feeding function. Therefore, the control unit 23 does not transmit the water feeding permission signal or the water feeding prohibition signal to the water feeding apparatus 30.

Next, the operation of the endoscope apparatus 1b formed as above is described.

Figure 13:
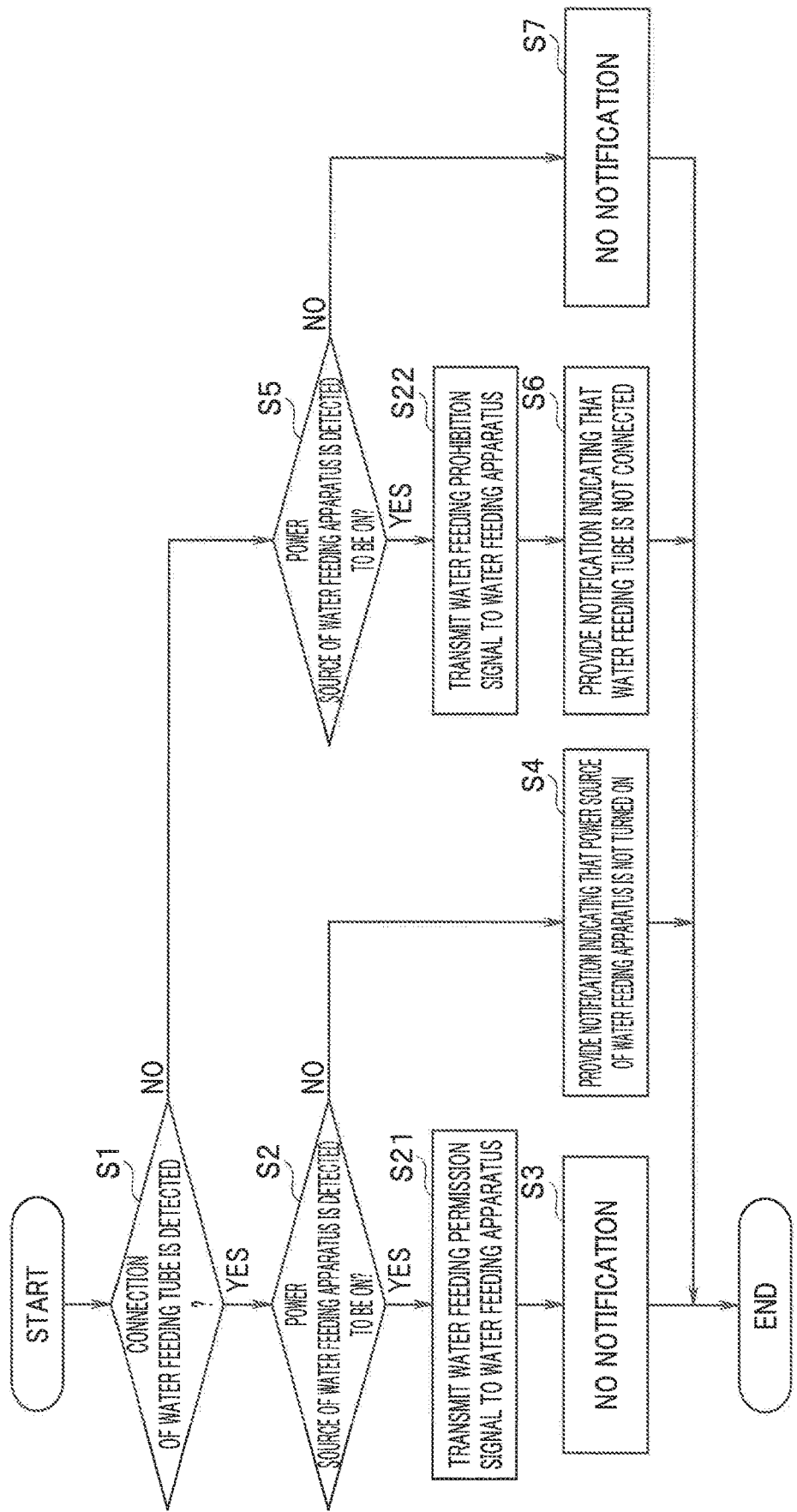
FIG. 13 is a flowchart illustrating an example of a flow of abnormality detection processing of the endoscope apparatus performed by the endoscope apparatus of Embodiment 3.

FIG. 13 is a flowchart illustrating an example of a flow of abnormality detection processing of the endoscope apparatus performed by the endoscope apparatus of Embodiment 3. Note that in FIG. 13, processing similar to the processing in FIG. 5 is denoted by the same reference characters and the description of the processing is omitted.

When the control unit 23 determines that the water feeding tube 33 is connected to the endoscope connector 14 in Step S1 and determines that the power source of the water feeding apparatus 30 is ON in Step S2, the control unit 23 transmits the water feeding permission signal to the water feeding apparatus 30 (S21).

When the control unit 23 determines that the water feeding tube 33 is not connected to the endoscope connector 14 in Step S1 and determines that the power source of the water feeding apparatus 30 is ON in Step S5, the control unit 23 transmits the water feeding prohibition signal to the water feeding apparatus 30 (S22).

As described above, in the endoscope apparatus 1b, when the water feeding tube 33 is not connected to the endoscope connector 14 and the power source of the water feeding apparatus 30 is ON, the water feeding prohibition signal is transmitted to the water feeding apparatus 30 from the control unit 23. As a result, in the endoscope apparatus 1b, even when the water feeding command signal is received from the foot switch 36 when the water feeding tube 33 is not connected to the endoscope connector 14 and the power source of the water feeding apparatus 30 is ON, the water feeding operation by the water feeding apparatus 30 can be prohibited and water can be prevented from being fed to unintended places.

Embodiment 4

Next, Embodiment 4 is described.

Figure 14:
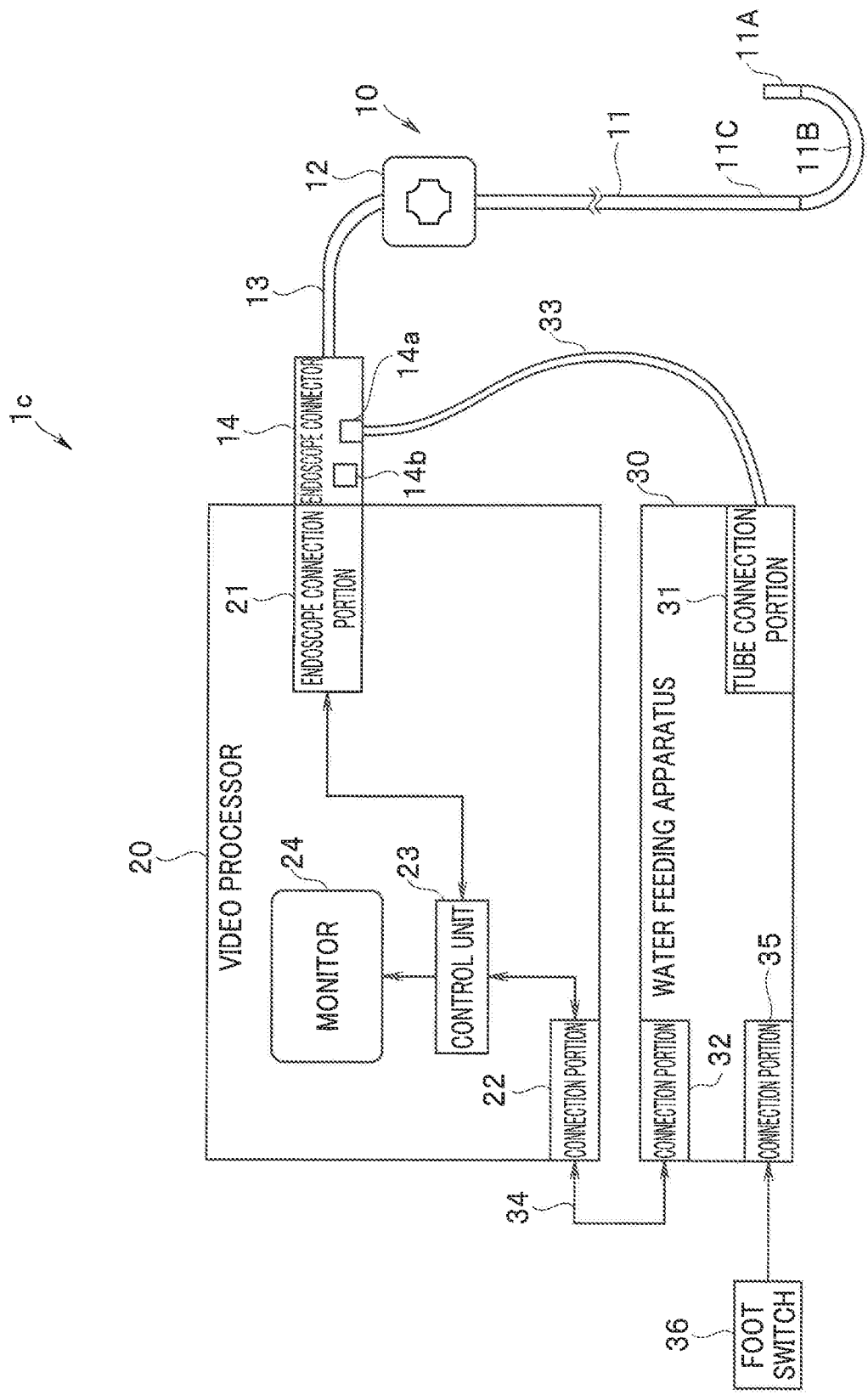
FIG. 14 is a configuration diagram illustrating a configuration of an endoscope apparatus according to Embodiment 4.

FIG. 14 is a configuration diagram illustrating a configuration of an endoscope apparatus according to Embodiment 4. Note that in FIG. 14, configurations similar to the configurations in FIG. 7 are denoted by the same reference characters and the description of the configurations is omitted.

As illustrated in FIG. 14, an endoscope apparatus 1c includes the connection portion 35 to which the foot switch 36 is connected in the water feeding apparatus 30. When the user performs an operation of pressing down the foot switch 36, the water feeding command signal is transmitted to the water feeding apparatus 30. The water feeding apparatus 30 controls the water feeding function to be used or not used based on the water feeding command signal transmitted from the foot switch 36.

The control unit 23 transmits the water feeding prohibition signal to the water feeding apparatus 30 according to whether there is a water feeding tube connection portion in the endoscope connector 14 and the information on ON/OFF of the power source of the water feeding apparatus 30.

Now, specific examples of whether there is a water feeding tube connection portion, the state of the power source of the water feeding apparatus 30, the type of the transmission signal, and the notification of abnormality are described with reference to FIG. 15. FIG. 15 is a diagram for describing a relationship among whether there is a water feeding tube connection portion, the state of the power source of the water feeding apparatus 30, the type of the transmission signal, and the notification of abnormality.

As illustrated in FIG. 15, the control unit 23 does not transmit the water feeding prohibition signal to the water feeding apparatus 30 when there is a water feeding tube connection portion in the endoscope connector 14.

When there is no water feeding tube connection portion in the endoscope connector 14 and the power source of the water feeding apparatus 30 is ON, the control unit 23 transmits the water feeding prohibition signal to the water feeding apparatus 30. When there is no water feeding tube connection portion in the endoscope connector 14 and the power source of the water feeding apparatus 30 is ON, there is a fear that water is fed to unintended places. Therefore, when there is no water feeding tube connection portion in the endoscope connector 14 and the power source of the water feeding apparatus 30 is ON, the control unit 23 transmits the water feeding prohibition signal to the water feeding apparatus 30.

When there is no water feeding tube connection portion in the endoscope connector 14 and the power source of the water feeding apparatus 30 is OFF, the control unit 23 does not transmit the water feeding prohibition signal to the water feeding apparatus 30. When the power source of the water feeding apparatus 30 is OFF, the water feeding apparatus 30 cannot execute the water feeding function. Therefore, the control unit 23 does not transmit the water feeding prohibition signal to the water feeding apparatus 30.

Next, the operation of the endoscope apparatus 1c formed as above is described.

Figure 16:
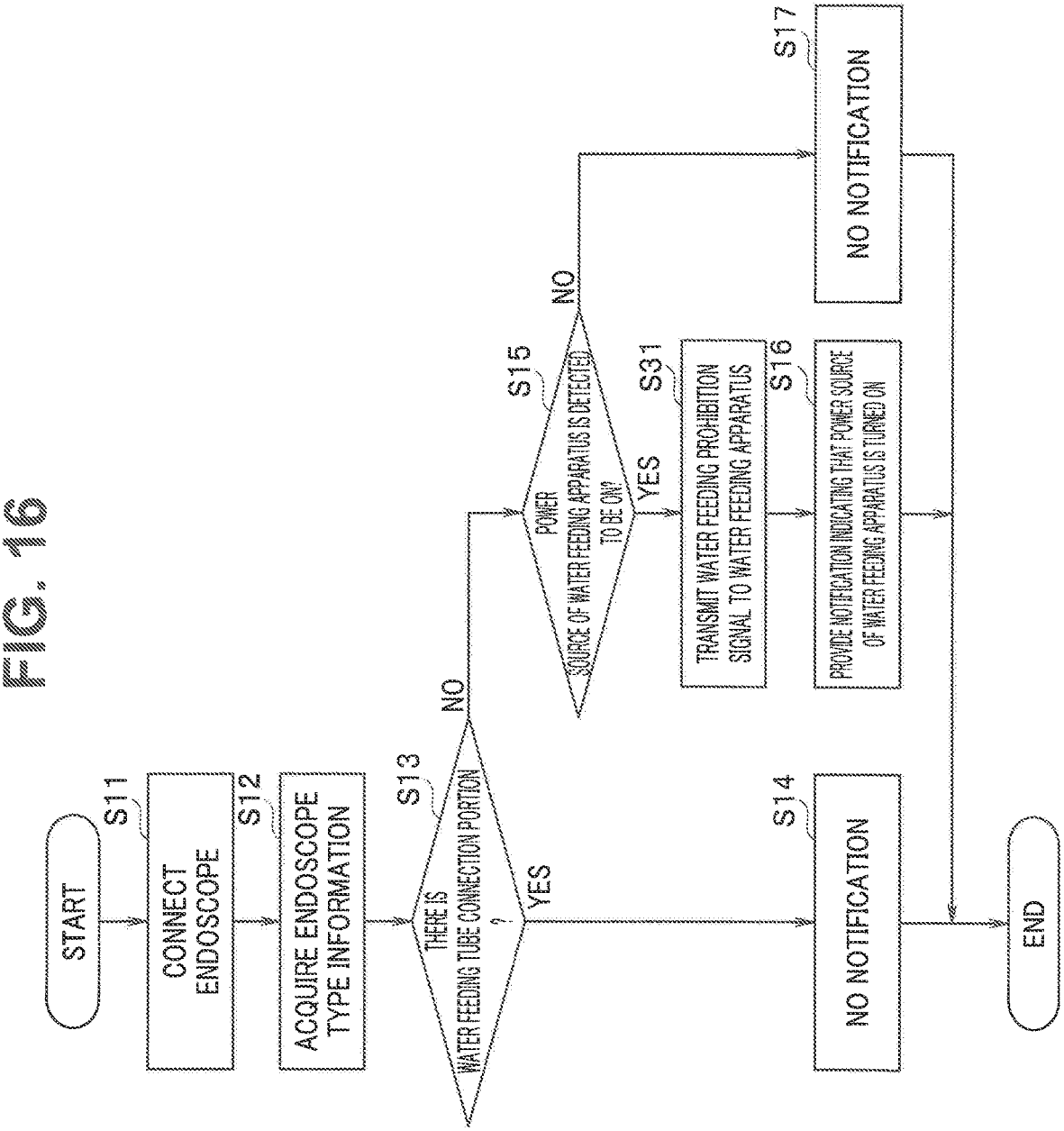
FIG. 16 is a flowchart illustrating an example of a flow of abnormality detection processing performed by the endoscope apparatus of Embodiment 4.

FIG. 16 is a flowchart illustrating an example of a flow of abnormality detection processing performed by the endoscope apparatus of Embodiment 4. Note that in FIG. 16, processing similar to the processing in FIG. 10 is denoted by the same reference characters and the description of the processing is omitted.

When the control unit 23 determines that there is no water feeding tube connection portion in Step S13 and determines that the power source of the water feeding apparatus 30 is ON in Step S15, the control unit 23 transmits the water feeding prohibition signal to the water feeding apparatus 30 (S31).

As described above, in the endoscope apparatus 1c, when there is no water feeding tube connection portion in the endoscope connector 14 and the power source of the water feeding apparatus 30 is ON, the water feeding prohibition signal is transmitted to the water feeding apparatus 30 from the control unit 23. As a result, in the endoscope apparatus 1c, even when the water feeding command signal is received from the foot switch 36 when the water feeding tube 33 is not connected to the endoscope connector 14 and the power source of the water feeding apparatus 30 is ON, the water feeding operation by the water feeding apparatus 30 can be prohibited and water can be prevented from being fed to unintended places.

Embodiment 5

Next, Embodiment 5 is described.

The configuration of an endoscope apparatus of Embodiment 5 is similar to the configuration of the endoscope apparatus 1a of Embodiment 2. In Embodiment 2, the control unit 23 does not provide the notification of abnormality when the control unit 23 determines that there is a water feeding tube connection portion in the endoscope connector 14.

In Embodiment 5, when the control unit 23 determines that there is a water feeding tube connection portion in the endoscope connector 14, the control unit 23 determines whether there is an abnormality according to the detection result from the connection detecting unit 14a and the ON/OFF information of the power source of the water feeding apparatus 30 and provides a notification of abnormality to the monitor 24. Note that when the control unit 23 determines that there is no water feeding tube connection portion in the endoscope connector 14, the control unit 23 provides the notification of abnormality according to ON or OFF of the power source of the water feeding apparatus 30 as with Embodiment 2.

Now, specific examples of whether there is a water feeding tube connection portion, the connection state of the water feeding tube 33, the state of the power source of the water feeding apparatus 30, and the notification of abnormality are described with reference to FIG. 17. FIG. 17 is a diagram for describing a relationship among whether there is a water feeding tube connection portion, the connection state of the water feeding tube 33, the state of the power source of the water feeding apparatus 30, and the notification of abnormality.

As shown in FIG. 17, when there is a water feeding tube connection portion in the endoscope connector 14, the control unit 23 provides the notification of abnormality according to whether the water feeding tube 33 is connected to the endoscope connector 14 and the ON or OFF of the power source of the water feeding apparatus 30.

More specifically, when the water feeding tube 33 is connected to the endoscope connector 14 and the power source of the water feeding apparatus 30 is ON, the control unit 23 does not provide the notification of abnormality. When the water feeding tube 33 is connected to the endoscope connector 14 and the power source of the water feeding apparatus 30 is OFF, the control unit 23 causes the monitor 24 to display the message informing the abnormality, that is, "power source of water feeding apparatus is not turned on".

When the water feeding tube 33 is not connected to the endoscope connector 14 and the power source of the water feeding apparatus 30 is ON, the control unit 23 causes the monitor 24 to display the message informing the abnormality, that is, "water feeding tube is not connected". When the water feeding tube 33 is not connected to the endoscope connector 14 and the power source of the water feeding apparatus 30 is OFF, the control unit 23 does not provide the notification of abnormality. Note that when there is no tube connection portion in the endoscope connector 14, the processing is similar to the processing in Embodiment 4, and hence the description of the processing is omitted.

Next, the operation of the endoscope apparatus 1a formed as above is described.

Figure 18:
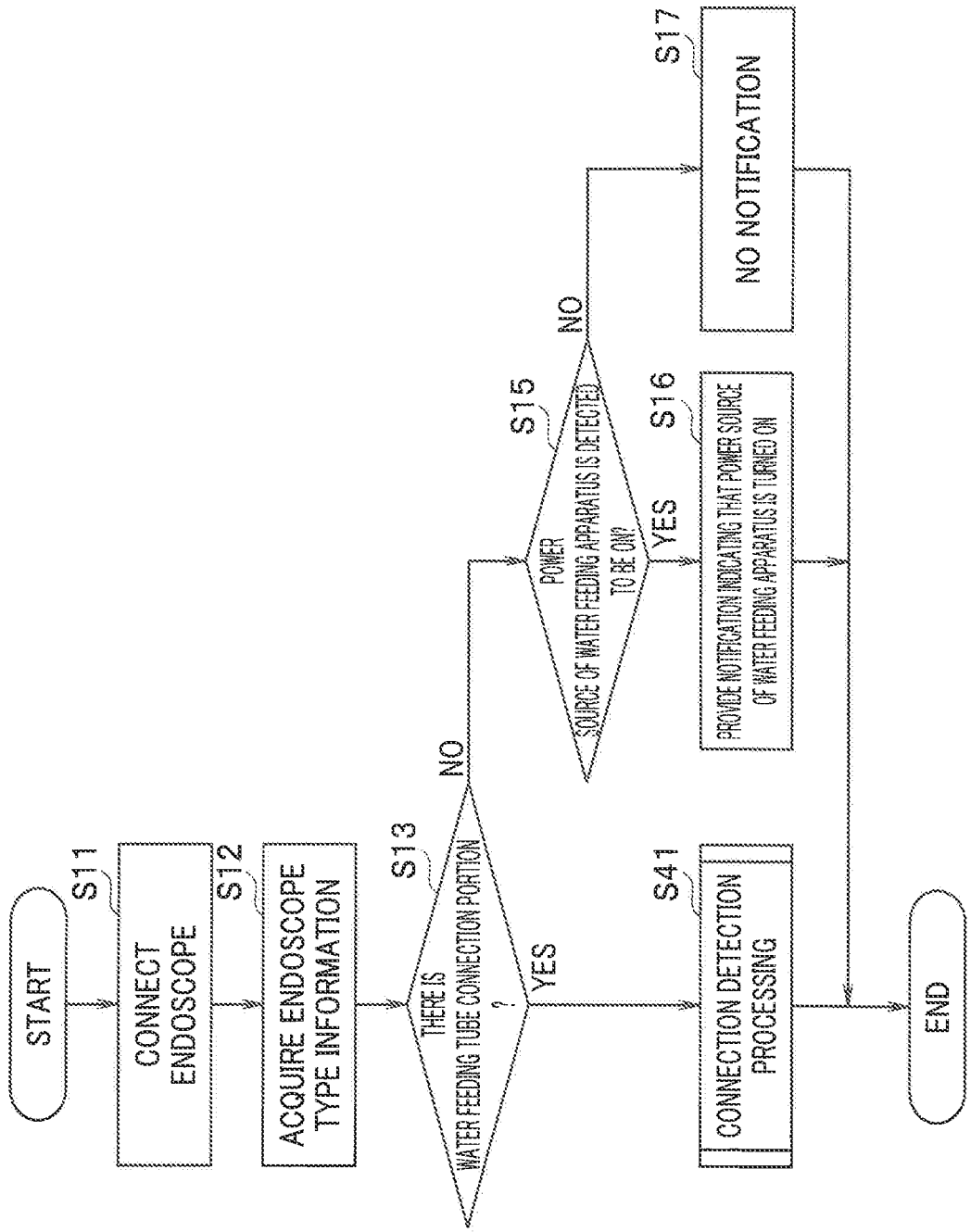
FIG. 18 is a flowchart illustrating an example of a flow of abnormality detection processing performed by the endoscope apparatus of Embodiment 5.
Figure 19:
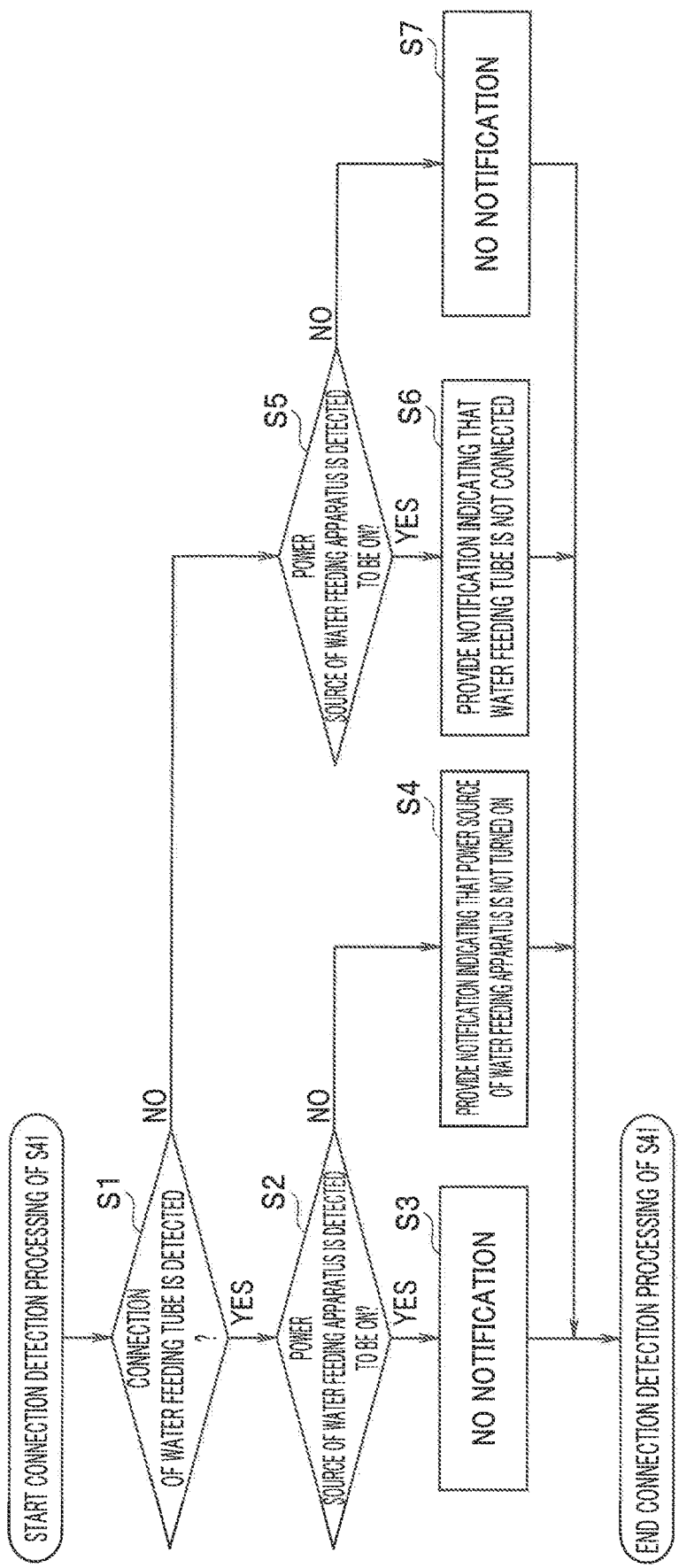
FIG. 19 is a flowchart illustrating an example of a flow of connection detection processing of Step S41 in FIG. 18.

FIG. 18 is a flowchart illustrating an example of a flow of abnormality detection processing performed by the endoscope apparatus of Embodiment 5, and FIG. 19 is a flowchart illustrating an example of a flow of connection detection processing of Step S41 in FIG. 18. Note that in FIG. 18, processing similar to the processing in FIG. 10 is denoted by the same reference characters and the description of the processing is omitted. In FIG. 19, processing similar to the processing in FIG. 5 is denoted by the same reference characters and the description of the processing is omitted.

As illustrated in FIG. 18, when the control unit 23 determines that there is a water feeding tube connection portion in Step S13, the control unit 23 executes the connection detection processing (S41). The connection detection processing in Step S41 is illustrated in FIG. 19. The connection detection processing in Step S41 is similar to the processing in FIG. 5, and the control unit 23 does not perform notification (S3) when the control unit 23 determines that the water feeding tube 33 is connected to the endoscope connector 14 (S1: YES) and determines that the power source of the water feeding apparatus 30 is ON (S2: YES).

When the control unit 23 determines that the water feeding tube 33 is connected to the endoscope connector 14 (S1: YES) and determines that the power source of the water feeding apparatus 30 is not ON (S2: NO), the control unit 23 provides a notification indicating that the power source of the water feeding apparatus 30 is not turned on (S4).

When the control unit 23 determines that the water feeding tube 33 is not connected to the endoscope connector 14 (S1: NO) and determines that the power source of the water feeding apparatus 30 is ON (S5: YES), the control unit 23 provides a notification indicating that the water feeding tube 33 is not connected (S6).

When the control unit 23 determines that the water feeding tube 33 is not connected to the endoscope connector 14 (S1: NO) and determines that the power source of the water feeding apparatus 30 is not ON (S5: NO), the control unit 23 does not perform notification (S7).

When the control unit 23 executes the processing in Step S3, Step S4, Step S6 or Step S7, the control unit 23 ends the connection detection processing in Step S41 and returns to FIG. 18. When the connection detection processing in Step S41 finishes in FIG. 18, the processing is ended.

As described above, in the endoscope apparatus 1a of the present embodiment, when there is a tube connection portion in the endoscope connector 14, the notification of abnormality is provided according to the connection state of the water feeding tube 33 and the ON/OFF state of the power source of the water feeding apparatus 30. As a result, water can be prevented from being fed to unintended places because the user can grasp the state of abnormality in a more accurate manner than in Embodiment 2.

Embodiment 6

Next, Embodiment 6 is described.

A configuration of an endoscope apparatus of Embodiment 6 is similar to the configuration of the endoscope apparatus 1c of Embodiment 4. In Embodiment 4, when the control unit 23 determines that there is a water feeding tube connection portion in the endoscope connector 14, the control unit 23 does not provide the notification of abnormality.

In Embodiment 6, when the control unit 23 determines that there is a water feeding tube connection portion in the endoscope connector 14, the control unit 23 transmits the water feeding permission signal or the water feeding prohibition signal to the water feeding apparatus 30 according to the detection result from the connection detecting unit 14a and the ON/OFF information of the power source of the water feeding apparatus 30. When the control unit 23 determines that there is a water feeding tube connection portion in the endoscope connector 14, the control unit 23 determines whether there is an abnormality according to the detection result from the connection detecting unit 14a and the ON/OFF information of the power source of the water feeding apparatus 30 and provides a notification of abnormality to the monitor 24. Note that when the control unit 23 determines that there is no water feeding tube connection portion in the endoscope connector 14, the control unit 23 transmits the water feeding prohibition signal and provides the notification of abnormality according to the ON or OFF of the power source of the water feeding apparatus 30 as with Embodiment 4.

Now, specific examples of whether there is a water feeding tube connection portion, the connection state of the water feeding tube 33, the state of the power source of the water feeding apparatus 30, the type of the transmission signal, and the notification of abnormality are described with reference to FIG. 20.

FIG. 20 is a diagram for describing a relationship among whether there is a water feeding tube connection portion, the connection state of the water feeding tube 33, the state of the power source of the water feeding apparatus 30, the type of the transmission signal, and the notification of abnormality.

As shown in FIG. 20, when there is a water feeding tube connection portion in the endoscope connector 14, the control unit 23 transmits the water feeding permission signal or the water feeding prohibition signal and provides the notification of abnormality according to whether the water feeding tube 33 is connected to the endoscope connector 14 and the ON or OFF of the power source of the water feeding apparatus 30.

More specifically, the control unit 23 transmits the water feeding permission signal to the water feeding apparatus 30 and does not provide the notification of abnormality when the water feeding tube 33 is connected to the endoscope connector 14 and the power source of the water feeding apparatus 30 is ON.

When the water feeding tube 33 is connected to the endoscope connector 14 and the power source of the water feeding apparatus 30 is OFF, the control unit 23 causes the monitor 24 to display the message informing the abnormality, that is, "power source of water feeding apparatus is not turned on". At that time, the control unit 23 does not transmit the water feeding permission signal or the water feeding prohibition signal to the water feeding apparatus 30 because the power source of the water feeding apparatus 30 is OFF.

When the water feeding tube 33 is not connected to the endoscope connector 14 and the power source of the water feeding apparatus 30 is ON, the control unit 23 transmits the water feeding prohibition signal to the water feeding apparatus 30 and causes the monitor 24 to display the message informing the abnormality, that is, "water feeding tube is not connected".

When the water feeding tube 33 is not connected to the endoscope connector 14 and the power source of the water feeding apparatus 30 is OFF, the control unit 23 does not provide the notification of abnormality. At that time, the control unit 23 does not transmit the water feeding permission signal or the water feeding prohibition signal to the water feeding apparatus 30 because the power source of the water feeding apparatus 30 is OFF. Note that when there is no tube connection portion in the endoscope connector 14, the processing is similar to the processing in Embodiment 4, and hence the description of the processing is omitted.

Next, the operation of the endoscope apparatus formed as above is described.

Figure 21:
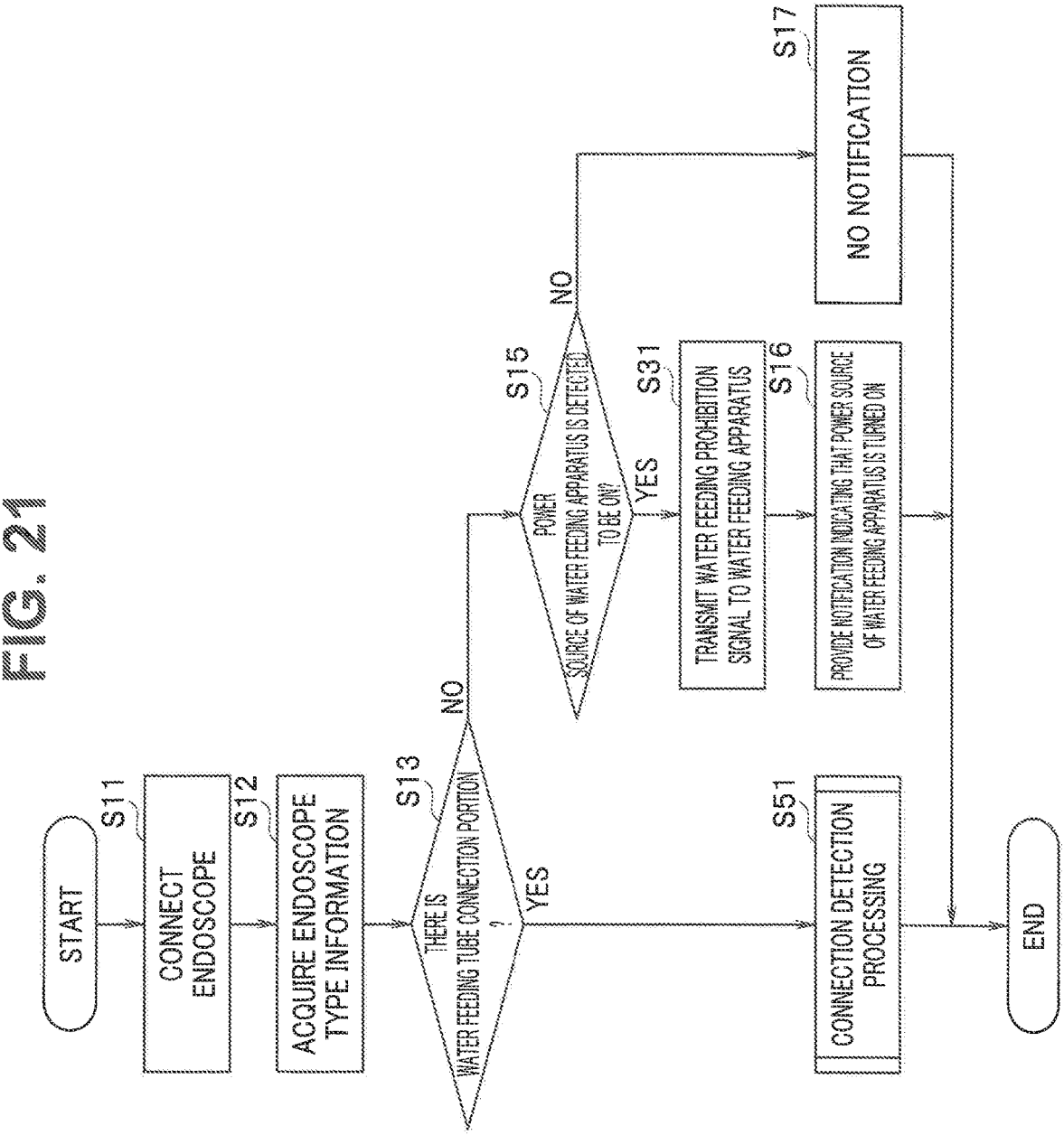
FIG. 21 is a flowchart illustrating an example of a flow of abnormality detection processing performed by an endoscope apparatus of Embodiment 6.
Figure 22:
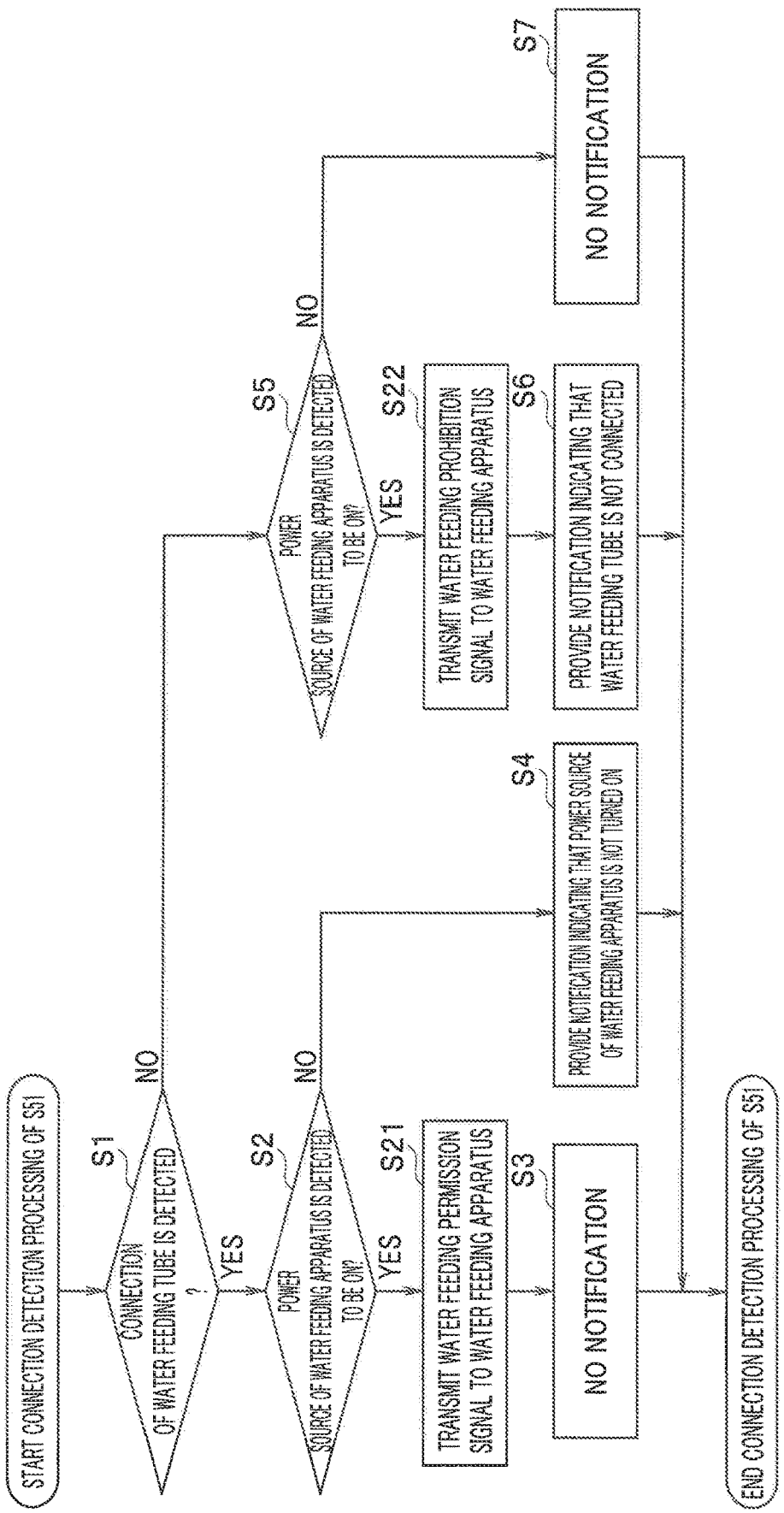
FIG. 22 is a flowchart illustrating an example of a flow of connection detection processing of Step S51 in FIG. 21.

FIG. 21 is a flowchart illustrating an example of a flow of abnormality detection processing performed by the endoscope apparatus of Embodiment 6, and FIG. 22 is a flowchart illustrating an example of a flow of connection detection processing in Step S51 in FIG. 21. Note that in FIG. 21, processing similar to the processing in FIG. 16 is denoted by the same reference characters and the description of the processing is omitted. In FIG. 22, processing similar to the processing in FIG. 13 is denoted by the same reference characters and the description of the processing is omitted.

As illustrated in FIG. 21, when the control unit 23 determines that there is a water feeding tube connection portion in Step S13, the control unit 23 executes the connection detection processing (S51). The connection detection processing in Step S51 is illustrated in FIG. 22. The connection detection processing in Step S51 is similar to the processing in FIG. 13, and the control unit 23 transmits the water feeding permission signal to the water feeding apparatus 30 (S21), and does not perform notification (S3) when the control unit 23 determines that the water feeding tube 33 is connected to the endoscope connector 14 (S1: YES) and determines that the power source of the water feeding apparatus 30 is ON (S2: YES).

When the control unit 23 determines that the water feeding tube 33 is connected to the endoscope connector 14 (S1: YES) and determines that the power source of the water feeding apparatus 30 is not ON (S2: NO), the control unit 23 provides a notification indicating that the power source of the water feeding apparatus 30 is not turned on (S4).

When the control unit 23 determines that the water feeding tube 33 is not connected to the endoscope connector 14 (S1: NO) and determines that the power source of the water feeding apparatus 30 is ON (S5: YES), the control unit 23 transmits the water feeding prohibition signal to the water feeding apparatus 30 (S22) and provides a notification indicating that the water feeding tube 33 is not connected (S6).

When the control unit 23 determines that the water feeding tube 33 is not connected to the endoscope connector 14 (S1: NO) and determines that the power source of the water feeding apparatus 30 is not ON (S5: NO), the control unit 23 does not perform notification (S7).

When the control unit 23 executes the processing in Step S3, Step S4, Step S6 or Step S7, the control unit 23 ends the connection detection processing in Step S51 and returns to FIG. 21. When the connection detection processing in Step S51 finishes in FIG. 21, the processing is ended.

As described above, in the endoscope apparatus 1c of the present embodiment, when there is a tube connection portion in the endoscope connector 14, the water feeding permission signal or the water feeding prohibition signal is transmitted and the notification of abnormality is provided according to the connection state of the water feeding tube 33 and the ON/OFF state of the power source of the water feeding apparatus 30. As a result, water can be prevented from being fed to unintended places because the user can grasp the state of abnormality in a more accurate manner than in Embodiment 4.

The exemplary embodiments are not limited to the above-mentioned embodiments, and various modifications, alterations, and the like can be made.

What is claimed is:

1. An endoscopic apparatus comprising:
a connector included in an endoscope and connected to an endoscope connection portion of a video processor;
a fluid feeding apparatus including a tube configured to transmit fluid to the endoscope;
a connection detector configured to detect a connection state of the tube with the connector of the endo scope;
a control processor configured to:
 detect an ON/OFF state of a power source of the fluid feeding apparatus;
 determine an abnormality exists when the connection detector detects that the tube is in a disconnected state with the connector of the endoscope and the power source of the fluid feeding apparatus is detected to be in an ON state; and
 output a notification of the determined abnormality; and
a display configured to display the notification of the abnormality outputted by the control processor.

2. The endoscopic apparatus according to claim 1, wherein the control processor is configured to transmit a prohibition signal to the fluid feeding apparatus prohibiting transmission of the fluid to the endoscope when the tube is detected to be disconnected from the connector and the power source of the fluid feeding apparatus is in the ON state.

3. The endoscopic apparatus according to claim 1, wherein the control processor is configured to:
determine a type of the endoscope, and
output the notification of the abnormality based on the determined type of the endoscope, the detected connection state of the tube with the connector of the endoscope, and the detected ON/OFF state of the power source of the fluid feeding apparatus.

4. The endoscopic apparatus according to claim 3, wherein the control processor is configured to transmit a prohibition signal to the fluid feeding apparatus prohibiting transmission of the fluid to the endoscope when the tube is determined to be unable to be connected to the connector based on the determined type of the endoscope and determining that the power source of the fluid feeding apparatus is in an ON state.

5. The endoscopic apparatus according to claim 1, wherein the control processor is configured to:
determine a type of the endoscope, and
transmit a prohibition signal to the fluid feeding apparatus prohibiting transmission of the fluid to the endoscope when the tube is determined to be unable to be connected to the connector based on the determined type of the endoscope and determining that the power source of the fluid feeding apparatus is in an ON state.

6. The endoscopic apparatus according to claim 1, further comprising memory including endoscope identification information, wherein the control processor is configured to determine a type of the endoscope based on the endoscope information stored in the memory.

7. The endoscopic apparatus according to claim 6, wherein the control processor is configured to output the notification of the abnormality based on the determined type of the endoscope, detecting that the tube is connected to the connector and determining that the power source of the fluid feeding apparatus is in an OFF state.

8. A video processor to which an endoscope and a water feeding apparatus configured to supply fluid to the endoscope are connected, the video processor comprising a control processor configured to communicate with the endoscope and the water feeding apparatus, the control processor being configured to:
acquire (i) information indicating whether a tube of the endoscope configured to supply the fluid from the water feeding apparatus is in a connected state or a disconnected state with respect to the endoscope and (ii) information on whether a power source of the water feeding apparatus is in an ON state or an OFF state,
determine an abnormality exists when the tube is in the disconnected state and the power source is in the ON state based on the acquired information, and
control a display to display a notification in response to determine that the abnormality exists.

9. An activation method of an endoscopic apparatus, the endoscopic apparatus including a connector included in an endoscope and connected to an endoscope connection portion of a video processor, and a fluid feeding apparatus including a tube connected to the connector and configured to supply fluid to the endoscope, the activation method comprising:
a step of transmitting the fluid to the endoscope via the tube by the fluid feeding apparatus;
a step of detecting a connection state of the tube with the connector by a connection detector;
a step of detecting an ON/OFF state of a power source of the fluid feeding apparatus by a control processor;
a step of determining an abnormality exists when the connection detector detects that the tube is in a disconnected state with the connector of the endoscope and the power source of the fluid feeding apparatus is detected to be in an ON state; and
a step of outputting a notification of the determined abnormality.

* * * * *